United States Patent [19]

Michel

[11] Patent Number: 5,694,932
[45] Date of Patent: Dec. 9, 1997

[54] SENSOR ARRAY

[75] Inventor: Peter Michel, Burgdorf, Switzerland

[73] Assignee: Disetronic Licensing AG, Burgdorf, Switzerland

[21] Appl. No.: 626,270

[22] Filed: Apr. 1, 1996

Related U.S. Application Data

[63] Continuation of Ser. No. 203,950, Mar. 1, 1994, abandoned.

[30] Foreign Application Priority Data

Mar. 1, 1993 [CH] Switzerland ............... 607/93

[51] Int. Cl.$^6$ ..................................... A61B 5/00
[52] U.S. Cl. ..................... 128/635; 204/403; 204/415
[58] Field of Search ..................... 128/632, 635, 128/637; 204/403, 415

[56] References Cited

U.S. PATENT DOCUMENTS

| | | | |
|---|---|---|---|
| 4,440,175 | 4/1984 | Wilkins | 128/635 |
| 4,545,382 | 10/1985 | Higgins et al. | 128/635 |
| 4,711,245 | 12/1987 | Higgins et al. | 128/635 |
| 4,963,245 | 10/1990 | Weetall | 204/403 |
| 5,171,689 | 12/1992 | Kawaguri et al. | 128/635 X |
| 5,322,063 | 6/1994 | Allen et al. | 128/634 X |
| 5,333,609 | 8/1994 | Bedingham et al. | 128/637 X |

FOREIGN PATENT DOCUMENTS

| | | |
|---|---|---|
| 0 122 420 | 6/1988 | European Pat. Off. . |
| 0 299778 | 1/1989 | European Pat. Off. . |
| 667 149 | 4/1991 | Switzerland . |
| 92/14741 | 9/1992 | WIPO . |
| WO 92/14836 | 9/1992 | WIPO . |

OTHER PUBLICATIONS

Lindner, Ernö, et al, "Flexible (Kapton–based) Microsensor Arrays of High Stability for Cardiovascular Applications", *Journal of the Chemical Society Faraday Transactions*, vol. 89, No. 2, (Cambridge, Great Britain) 1993, pp. 361–367.

*Primary Examiner*—Jennifer Bahr
*Assistant Examiner*—Eric F. Winakur
*Attorney, Agent, or Firm*—Walter C. Farley

[57] ABSTRACT

A sensor is used to detect a substance component in an aqueous solution. This sensor has electrically conducting and mutually insulated electrodes (7) which can be connected to a data-recording device. A sensor membrane array responsive to substance components to be detected includes several individual membranes (2) in rows or row-column arrays mounted on a flat support (1).

8 Claims, 2 Drawing Sheets

5,694,932

SENSOR ARRAY

This is a continuation of application Ser. No. 08/203,950 filed Mar. 1, 1994 and now abandoned.

FIELD OF THE INVENTION

This invention relates to a sensor for selectively detecting or measuring at least one substance component in an aqueous solution.

BACKGROUND OF THE INVENTION

Sensors of the general type to which the invention relates have been used in large numbers in chemical engineering, in analysis and more recently also in medicine. In medicine in particular there is a great demand for such so-called biosensors. Biosensors are most widely used in diabetes therapy. Examples are found in U.S. Pat. Nos. 4,545,382 and 4,711,245, Higgins. Essentially, they consist of disposable gluco-sensors onto which a small quantity of blood to be analyzed is deposited and which are plugged into a measuring device (glucometer). The user conventionally withdraws the required blood by piercing a finger tip. When the gluco-sensor is inserted into the measuring device, the bio-membrane of the sensor makes electrical contact with the device as a result of which voltage and/or current changes in the active bio-membrane caused by the different glucose contents are transmitted to the measuring device. Further details of such known glucometers and gluco-sensors are discussed in Graetzel et al WO92/14,836.

All the known sensors of this kind incur the drawback of short life and comparatively costly manufacture. In particular it was found that the gluco-sensor's membrane, of which the active ingredient is an unstable enzyme such as glucose oxidase, on one hand is difficult to reproducibly manufacture and on the other hand its properties change with age so that its usable life is much degraded. Examples of such enzymes and combinations of them with a mediator are given in the Graetzel et al documents WO92/14,836 and WO92/14,741.

SUMMARY OF THE INVENTION

An object of the invention is to create a sensor for detecting an electrical current produced by reaction with the sensor to evaluate chemical substances participating in the reaction which evinces extended life and at the same time is substantially more economical to manufacture.

Instead of providing the patient with a pack of several hundred disposable individual sensors, a single sensor may be used which comprises a plurality of individual sensor membranes mounted in rows or a matrix of row-column arrays on a flat substrate.

The advantages achieved by the invention essentially are that very economical manufacture is made possible by the sensor of the invention and in that its useful life is extended.

BRIEF DESCRIPTION OF THE DRAWIGNS

Preferred embodiments of the invention are described below with reference to the following drawings wherein.

DESCRIPTION OF THE PREFFERED EMBODIMENTS

Figure 1:
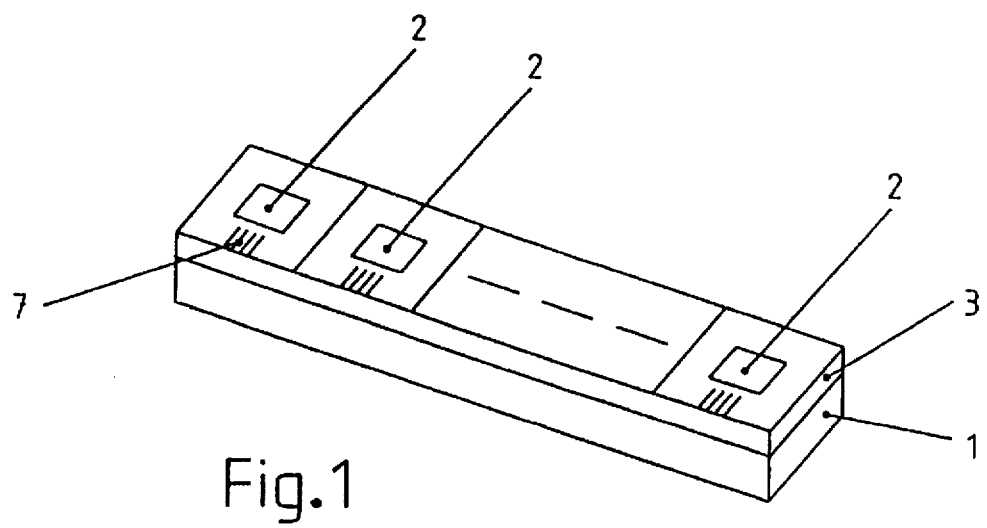
FIG. 1 is a perspective view of a sensor in accordance with the invention with sensor membranes along a linear measuring strip.
Figure 2:
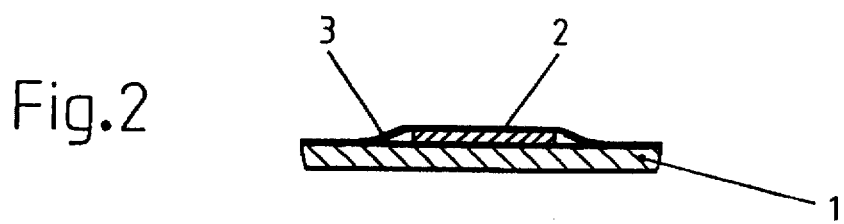
FIG. 2 is a transverse sectional view of the sensor of FIG. 1.

A sensor assembly in accordance with the invention is shown in FIG. 1 and comprises an elongated and flat substrate 1 of plastic such as polyvinyl chloride (PVC) on which several individual sensor membranes 2 are mounted in a row and are covered by a removable aluminum foil 3 protecting them against external influences. Each individual membrane 2 essentially consists of an enzyme-mediator combination capable of responding to the substance component which must be detected and, by means of a set of electrodes 7 mounted laterally of each membrane on the longitudinal substrate 1, the adjacent membrane can be connected to a data-recording or display device 4 as shown schematically in FIG. 3. Basically the set of electrodes 7 includes at least two, but preferably three, mutually insulated electrodes, including an operating electrode, a monitoring electrode and a reference electrode, the latter preferably being made of silver. If only two sensors are provided, the reference and monitoring electrodes are combined into one.

To activate an individual membrane 2, it suffices to manually remove the part of the protective layer over it, for instance by tearing it off, piercing or punching it, and to deposit thereon the aqueous solution, for instance a blood drop, to be tested.

Figure 3:
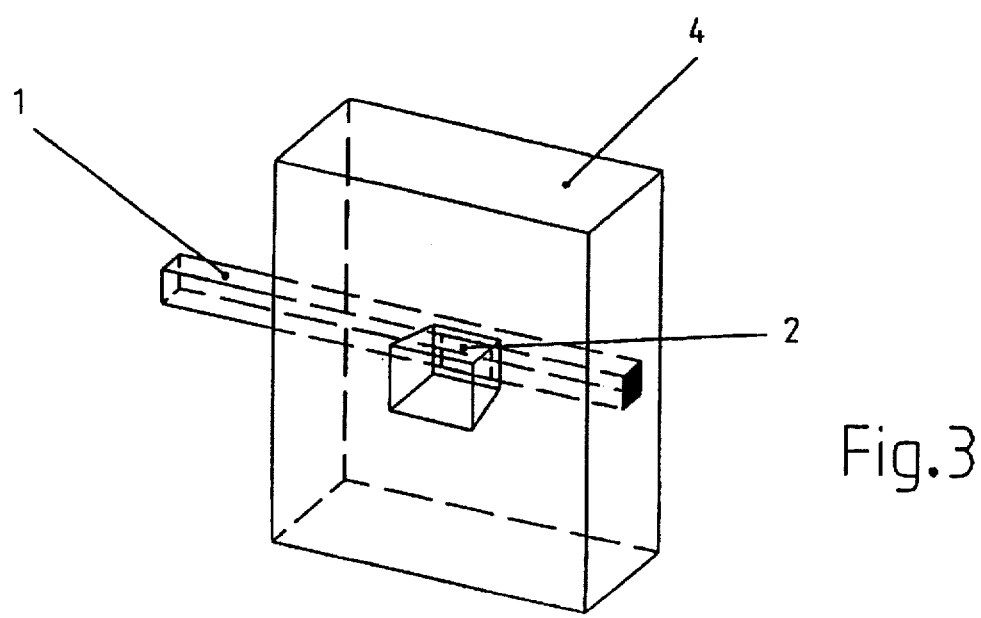
FIG. 3 is a schematic view of a typical measuring device with a sensor in accordance with FIG. 1 inserted therein.

Thereupon the sensor assembly with the individual membranes 2 arranged in a row can be inserted in a known manner into a data-recording and display device 4 schematically shown in FIG. 3. The sensor activation can be implemented in several ways. One way is to insert the sensor assembly into the data-recording and display device 4 until the selected individual sensor membrane 2 makes contact by its electrodes 7 with sensor electronics, not shown, of the data-recording and display device 4. Another way, applicable especially to sensors implanted into the bodies of patients, is to control the next individual membrane 2 to be activated by the sensor electronics of the data-recording and display device 4 itself. More details on data-recording and display device 4 as well as on the construction of individual membranes 2 will be found in the Swiss Michel patent 677,149 which is hereby incorporated by reference.

As regards sensors outside the body, used individual membranes 2 may be simply broken off and discarded.

Figure 4:
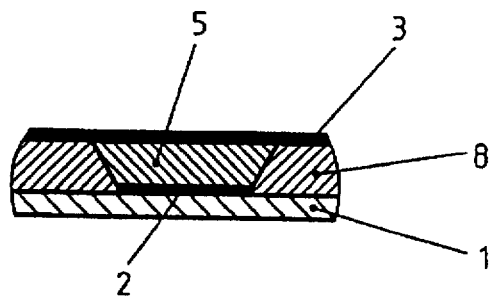
FIG. 4 is a transverse sectional view of a further embodiment of a sensor in accordance with the invention.

A somewhat more complex sensor assembly is shown in FIG. 4, where a substrate 1 supports a plastic substrate layer 8 into which are integrated a plurality of individual membranes 2, again mounted in a row, together with a superposed calibration liquid 5 and a removable aluminum foil layer 3 providing protection against external effects and covering this assembly. Calibration liquid 5 includes a neutral salt solution and performs several functions. In the first place, it allows storing the individual membranes 2 in a defined environment and in the second place it allows calibrating when starting the data-recording and display device 4. The third function, which is particularly advantageous for the invention, is that by heating the calibration liquid 5, similarly to an ink-jet printer, the protective layer 3 can be burst open by internal energy provided by the vapor pressure of the liquid to remove the foil and activate the individual membranes 2 for measurement.

For design reasons, a further plastic substrate layer 8 is mounted on the substrate I for the embodiment of the calibration solution 5 of FIG. 4, and the protective layer 3 rests on substrate layer 8.

Figure 5:
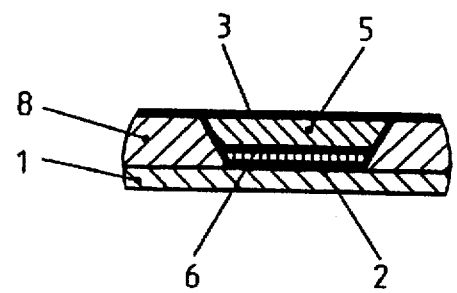
FIG. 5 is a transverse sectional view of another embodiment of a sensor in accordance with the invention.

FIG. 5 shows another embodiment of the sensor of FIG. 4, wherein an absorbent foil or cover 6 is between each individual membrane 2 and the calibration liquid to optimize the distribution of the aqueous solution to be measured. A nylon netting or porous foil may be used as absorbent cover 6, the purpose of which is to retain and spread a small amount of liquid.

Figure 6:
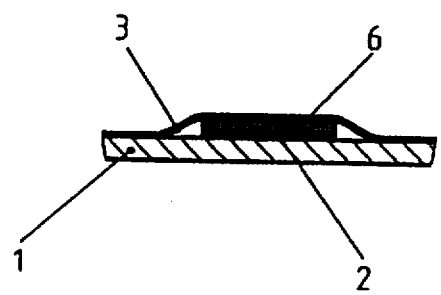
FIG. 6 is a transverse sectional view of yet another embodiment of a sensor in accordance with the invention.

FIG. 6 shows a preferred embodiment of the sensor of the invention in which the individual membranes 2 together with a superposed suction duct 6 covered by the protective foil 3 are mounted on the substrate 1. This is the least expensive and simplest of the embodiments.

Figure 7:
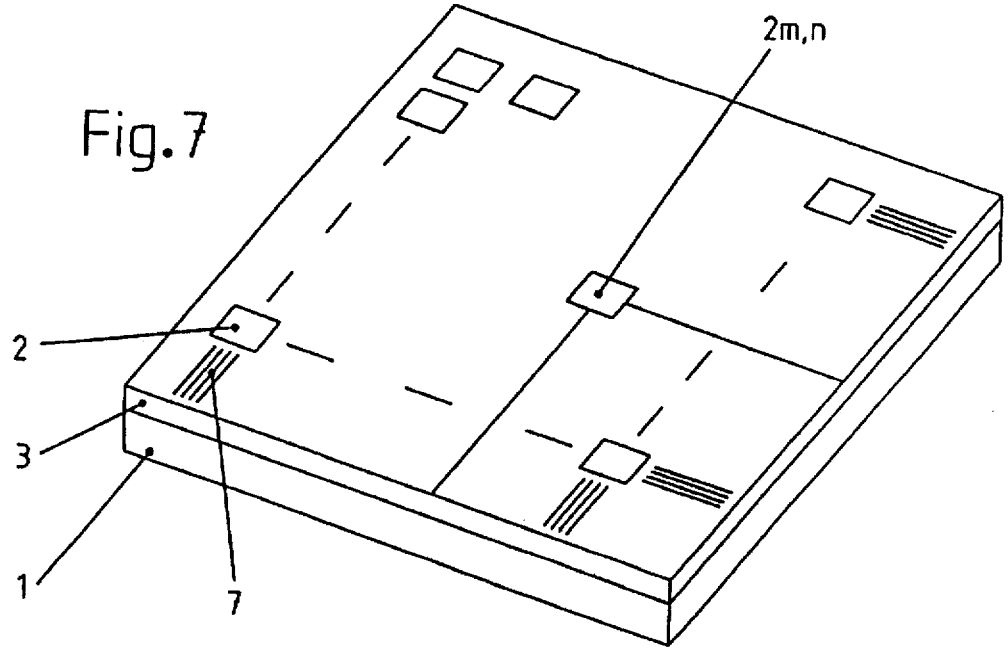
FIG. 7 is a perspective view of a sensor in accordance with the invention in the form of a row-column matrix.

FIG. 7 shows a sensor in the form of a multi-row array of individually mounted individual membranes $2_{m,n}$ (individual membrane of the mth row and nth column). This array is especially suitable for implant sensors in which individual membranes 2 to be activated are directly controlled by data-recording and display device 4 electronics also making the calibration liquid 5 boil.

What is claimed is:

1. An array of sensors for selectively detecting or measuring at least one substance component in an aqueous solution, comprising
   a flat substrate (1);
   a plurality of sets of electrically conductive and mutually insulated electrodes (7) on said substrate connectable to a data-recording and display device (4);
   an array of individual sensor membranes each responsive to a component of a substance to be detected or measured, said array of individual sensor membranes (2) being arranged on said flat substrate (1) with one membrane adjacent each set of electrodes;
   a protective layer covering and protecting said membranes against external influences;
   a calibration solution (5) between said individual membranes and said protective layer; and
   an absorbent cover mounted on each of said individual membranes.

2. A sensor according to claim 1 wherein said protective layer is removable and comprises a metal foil.

3. A sensor according to claim 1 wherein said calibration solution comprises a neutral salt solution.

4. A sensor according to claim 1 wherein each of said individual membranes (2) contains an enzyme responsive to the substance component to be detected.

5. A sensor according to claim 4 wherein, in addition to said enzyme, each of said individual membranes (2) comprises a mediator.

6. A sensor according to claim 1 wherein each of said individual membranes (2) responds to physiological substances in the body fluids.

7. A sensor according to claim 6 wherein a fluid to which said membrane responds is glucose.

8. A sensor according to claim 1 wherein said electrodes (7) include three mutually insulated electrodes including an operational electrode, a monitoring electrode, and a reference electrode, said reference electrode being made of silver.

* * * * *